(12) United States Patent
Soderlund

(10) Patent No.: US 7,988,557 B2
(45) Date of Patent: Aug. 2, 2011

(54) METHOD FOR PLAYING GAMES USING BRAIN WAVES

(75) Inventor: Staffan Soderlund, Kista (SE)

(73) Assignee: Interactive Productline AB, Kista (SE)

( * ) Notice: Subject to any disclaimer, the term of this patent is extended or adjusted under 35 U.S.C. 154(b) by 71 days.

(21) Appl. No.: 10/596,862

(22) PCT Filed: Nov. 29, 2004

(86) PCT No.: PCT/SE2004/001778
§ 371 (c)(1), (2), (4) Date: Jun. 27, 2006

(87) PCT Pub. No.: WO2005/065794
PCT Pub. Date: Jul. 21, 2005

(65) Prior Publication Data
US 2007/0123350 A1    May 31, 2007

Related U.S. Application Data

(60) Provisional application No. 60/481,850, filed on Jan. 2, 2004.

(51) Int. Cl.
*A63F 9/00* (2006.01)
(52) U.S. Cl. ............................................. 463/36
(58) Field of Classification Search ............... 463/63
See application file for complete search history.

(56) References Cited

U.S. PATENT DOCUMENTS

| | | | | |
|---|---|---|---|---|
| 3,712,617 A | * | 1/1973 | Ohlschlager | 273/153 R |
| 3,811,676 A | * | 5/1974 | Greenberg | 273/110 |
| 4,332,385 A | * | 6/1982 | McCaslin | 273/113 |
| 4,674,749 A | * | 6/1987 | Shaffer et al. | 273/153 R |
| 4,743,023 A | * | 5/1988 | Collier | 273/113 |
| 5,145,174 A | * | 9/1992 | Caramanoff | 273/109 |
| 5,213,338 A | * | 5/1993 | Brotz | 273/460 |
| 5,638,826 A | * | 6/1997 | Wolpaw et al. | 600/544 |
| 5,772,508 A | * | 6/1998 | Sugita et al. | 463/36 |
| 6,001,065 A | * | 12/1999 | DeVito | 600/544 |

FOREIGN PATENT DOCUMENTS

| | | |
|---|---|---|
| EP | 0177075 A2 | 4/1986 |
| JP | 10-76072 | 3/1989 |
| WO | WO 01/07128 A1 * | 2/2001 |

OTHER PUBLICATIONS

Samurai Shodown. Released Aug. 11, 1993. <http://www.gamefaqs.com/console/neogeo/review/R127911.html>.*
English translation of JP 10-076072.*
International Search Report mailed Mar. 17, 2005, PCT Application No. PCT/SE2004/001778 filed Nov. 29, 2004, 2 pages.

* cited by examiner

*Primary Examiner* — Peter DungBa Vo
*Assistant Examiner* — Seng Heng Lim
(74) *Attorney, Agent, or Firm* — Morrison & Foerster LLP

(57) ABSTRACT

The method is for playing a game by providing each player with a sensor for measuring brain wave frequencies of the players. The player moves a unit on a playing area in an x-direction toward the player when the brain wave frequency of the player is at a first frequency and the brain wave frequency of the player is at a second frequency wherein the first frequency is lower than the second frequency. The player moves the unit in a y-direction perpendicular to the x-direction when the brain wave frequency of the player is at a third frequency and the brain wave frequency of the player is at a fourth frequency wherein the third frequency is greater than the fourth frequency.

11 Claims, 2 Drawing Sheets

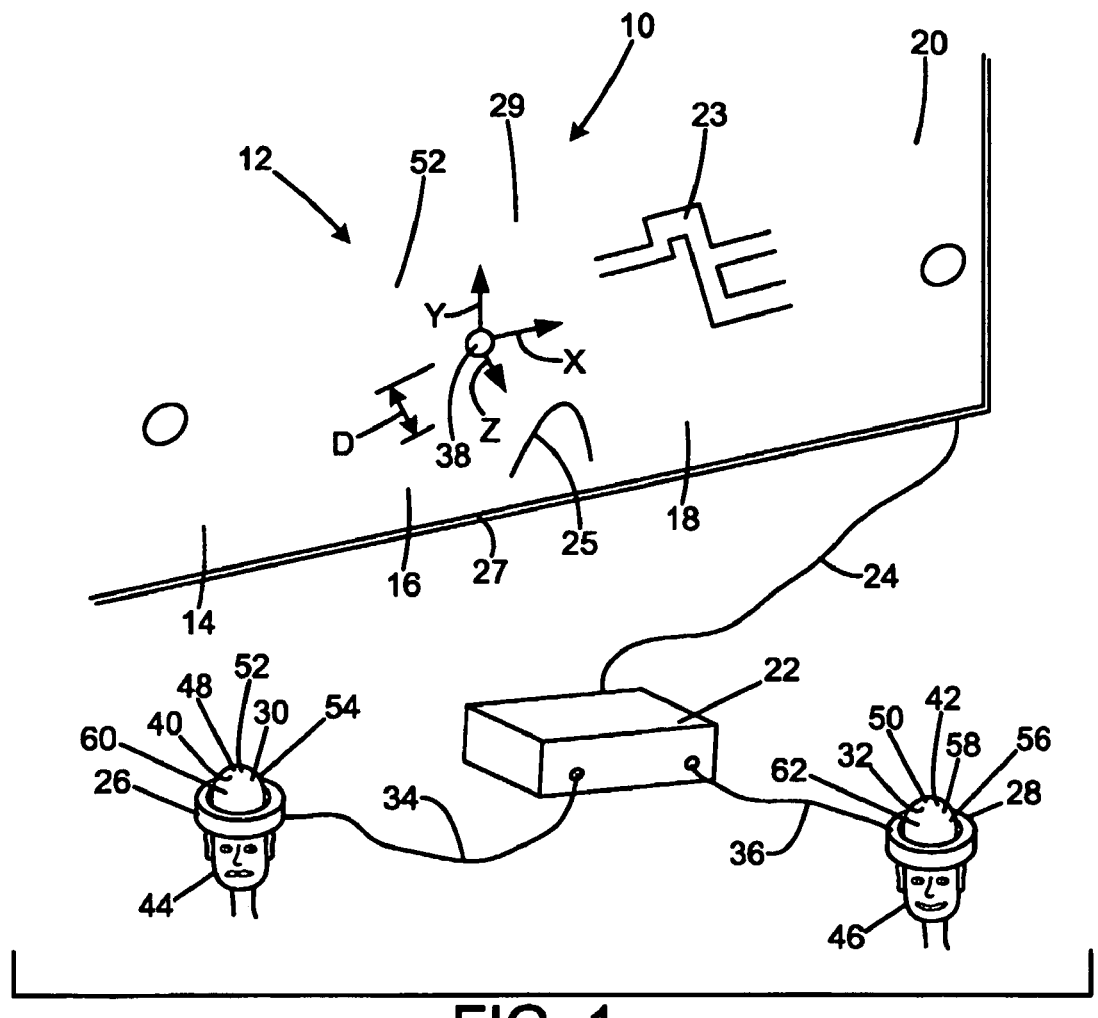
FIG. 1
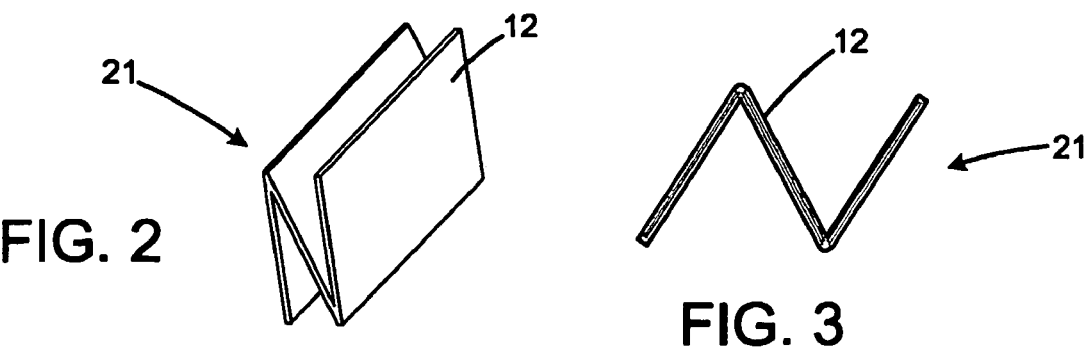
FIG. 2
FIG. 3

METHOD FOR PLAYING GAMES USING BRAIN WAVES

PRIOR APPLICATION

This application is a U.S. national phase application based on International Application No. PCT/SE2004/001778, filed 29 Nov. 2004, claiming priority from U.S. Provisional Patent Application No. 60/461,850, filed 2 Jan. 2004.

TECHNICAL FIELD

The present invention relates to a method for playing a game, such as a ball game, by measuring brain wave frequencies to move a ball on a magnetic playing area.

BACKGROUND OF THE INVENTION

In today's society people are becoming more and more stressed due to increased pace in life. Some of the stress is related to increased use of the brain at relatively high wave frequencies such as when a person is agitated. The injuries and reduced quality of life related to stress could be reduced if people could improve their ability to control the brain wave frequencies so that the brain operates more at lower brain wave frequencies. There is a need for an effective and stimulating way of learning to control the brain wave frequencies to, among other things, lower the stress level.

SUMMARY OF THE INVENTION

The method of the present invention provides a solution to the above-outlined problems. More particularly, the method of the present invention is for playing a game by providing each player with a sensor for measuring brain wave frequencies of the players. The first player may move a unit on a playing area in an x-direction toward the second player when the brain wave frequency of the first player is at a first frequency and the brain wave frequency of the second player is at a second frequency wherein the first frequency being lower than the second frequency. The first player may move the unit in a y-direction perpendicular to the x-direction when the brain wave frequency of the first player is at a third frequency and the brain wave frequency of the second player is at a fourth frequency wherein the third frequency being greater than the fourth frequency. The first player may also move the unit in the x-direction due to a lower brain wave frequency compared to the second player while the second player moves the unit in the y-direction due to a brain wave frequency that is higher than a trigger value for moving the unit in the y-direction.

BRIEF DESCRIPTION OF THE DRAWING

FIG. 1 is a schematic view of a playing area of the game of the present invention;

FIG. 2 is a schematic perspective view of the playing area in a folded position menu of the present invention;

FIG. 3 is an elevational side view of the playing area in a partially folded position:

DETAILED DESCRIPTION

Figure 4:
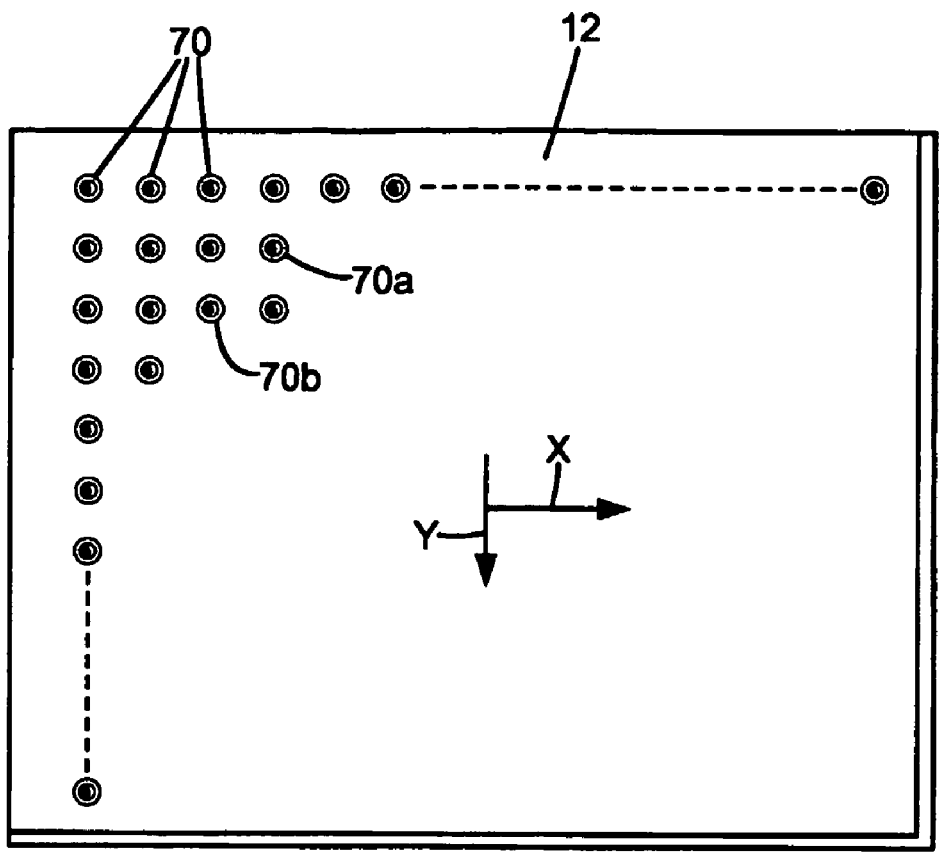
FIG. 4 is a top view of the playing area.

With reference to FIGS. 1-6, the method and game 10 of the present invention has a portable rectangular shaped playing area 12 that may include four segments 14, 16, 18, 20. The area 12 may be made of a rubber material or any other suitable material. The segments 14 and 20 may be considered goal segments and may or may not include instruments that could be used to control a ball and other functions of the playing area.

The playing area 12 may be folded into a compact unit 21, as best shown in FIGS. 2-3, so that it is easy to carry and transport. The playing area 12 may be connected by a wire 24 to a computer and control electronics unit 22. The area 12 may also communicate with the unit 22 by using wireless technology. A pair of headbands 26, 28 including biosensor units 30, 32, respectively may be connected to the unit 22 either by wires 34, 36 or by wireless technology.

The game 10 may have a magnetic ball 38 or any other item that may be moved in the x-direction and/or the y-direction depending upon brain-wave frequencies 40, 42 of players 44, 46, respectively, are measured by the sensors units 30, 32 in the headbands 26, 28 that are put over the heads 48, 50 of the players 44, 46. The ball 38 may float a distance (D) above an upper surface area 52 in a z-direction that gives an illusion of zero-gravity. Of course, the ball 38 may roll on the surface 52 also. Preferably, the movement of the ball 38 in the z-direction is not a variable. However, in a three dimensional variation of the game, the z-direction is a variable also.

In operation, the playing area 12 is placed on an even surface such as a table. The player 44 may sit behind the segment 14 while the player 46 sits on the opposite side behind the segment 20. With the headbands 26, 28 placed on the heads 48, 50 of each player 44, 46, the brain wave frequencies of the players may move the ball 38 in both the x-direction and in the y-direction. For example, theta wave frequencies 52 and alpha wave frequencies 54 of the player 44 are measured by the sensor 30 and sent to the unit 22 via the wire 34 for processing. Simultaneously, theta wave frequencies 56 and alpha wave frequencies 58 of the player 46 are measured by the sensor 32 and sent to the unit 22 via the wire 36 for further processing. The theta wave frequencies 52, 56 may range from 3-8 Hz while the alpha wave frequencies 54, 58 may range from 8-12 Hz. In general, the lower the frequencies the calmer the player is. The sensors 30, 32 may be connected to a biosensor system that registers the electrical activity of the brains of the players. Electro-Encefalo-Grafi (EEG) may be used to measure the brain wave frequencies.

The processor 22 may be programmed so that the ball 38 moves in the x-direction towards the player with the highest theta and alpha wave frequency. In other words, the calmest player is likely to win the game when the ball 38 moves into the segment 14 or 20. It is also possible to control the speed of the ball 38 so that the ball 38 has a first high velocity when the brain wave frequency is close to 3 Hz and a second lower velocity when the brain wave frequency is approaching 12 Hz so that the velocity of the ball 38 increases with reduced brain wave frequency. The game 10 could also be designed so that the velocity of the ball 38 increases with increased brain wave frequency up to 12 Hz. Of course, the velocity of the ball 38 may vary continuously with the change of the brain wave frequency. When the brain wave frequency exceeds 18 Hz, the direction of the ball 38 changes to the y-direction as described below.

It is also possible to move the ball 38 in the y-direction by measuring beta wave frequencies 60, 62 of the players 44, 46. The beta wave frequencies 60, 62 may be waves over 18 Hz. In this way, a player can thus affect the movement of the ball 38 in the y-direction by intensifying the brain activity. The rule of the game 10 may be such that if the ball 38 rolls off at the edges 27, 29 of the play area 12 in the y-direction, the player with the lowest brain activity either wins or loses.

This means that if a player is agitated and the brain wave frequency increases way over the 18 Hz limit, the player may start moving the ball 38 towards one of the edge 27, 29 and lose the game. The movement in the y-direction may occur if one or both players have brain wave frequencies over 18 Hz. When both players have frequencies exceeding 18 Hz, the ball may move in the direction that is to the detriment of the player with the highest frequency. As indicated earlier, the rule may be so that one of the players loses the game when the ball goes over the edge 27, 29 in the y-direction.

The playing area 12 may be flat or be a labyrinth 23 with several paths so that the player must move in both the x-direction and in the y-direction in order to navigate a ball from one end to another of the labyrinth.

The playing area 12 may also have a virtual uphill 25 so that the game 10 requires a certain velocity of the ball 38 to roll over the virtual hill. The playing area 12 may also be three-dimensional so that the z-direction is a variable also.

It is possible to connect the unit 22 to an external computer that includes a monitor that shows the brain wave frequency of each player during the game.

Figure 5:
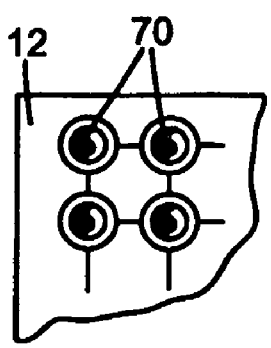
FIG. 5 is a detailed top view of the playing area showing control connections.
Figure 6:
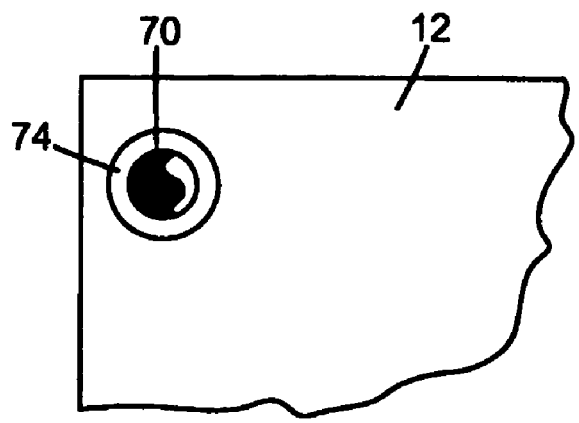
FIG. 6 is a detailed top view of a control connection.

With reference to FIGS. 4-6, the playing area 12 has a plurality of repelling permanent magnet units 70 so that the ball 38 is repelled by the magnets and floating in the air. By controlling the amount of attracting forces induced by the magnetism generated by a coil 74, the ball may be moved while the permanent magnet 70 maintains the distance (D) to the floating ball 38 that may move in either the x-direction or the y-direction of the playing area 12. For example, by reducing a repelling force of the coils surrounding a magnet 70a compared to a magnet 70b, the ball will move in the direction of the magnet 70a. The unit 22 may be used to control the magnetism induced by the coil 74 of each magnet unit 70 based on the brain wave frequency of the players 44, 46 as described above.

In this way, the ball 38 may simultaneously move both in the x-direction and the y-direction when one player has a brain wave frequency exceeding 18 Hz to trigger the movement of the ball 38 in the y-direction while the other player may move the ball 38 in the x-direction as long as the second player has a brain wave frequency below 12 Hz since that only triggers movement of the ball 38 in the x-direction. The second player can either win by moving the ball 38 in the x-direction into the segment 14, 20 or the first player moves the ball 38 over one of the edges 27, 29 in the y-direction.

By learning to control the brain wave frequency of the brain by bio-feedback, the player may better be able to put him/herself in a more relaxed condition.

While the present invention has been described in accordance with preferred compositions and embodiments, it is to be understood that certain substitutions and alterations may be made thereto without departing from the spirit and scope of the following claims.

The invention claimed is:

1. A computer-implemented method for playing a game, the method comprising:
providing a first player with a sensor and a second player with another sensor for measuring brain wave frequencies of the players, wherein the sensors are in communication with a processor;
the processor is configured to receive inputs from the sensors and outputs a command so that a unit rolls on top of a playing area in an x-direction toward a goal area of a the first player when the brain wave frequency of the first player is between 3-12 Hz and the brain wave frequency of the first player is below a brain wave frequency of the second player, wherein moving the unit into the goal area of the first player establishes the first player as the winner of the game, and
the first player increasing a velocity of the unit by lowering the brain wave frequency of the first player towards 3 Hz.

2. The method according to claim 1 wherein the unit is a magnetic unit and the method further comprises floating the unit a distance (D) over the playing area.

3. The method according to claim 1 wherein the method further comprises measuring theta wave, alpha wave and beta wave frequencies of the brains of the players.

4. The method according to claim 1 wherein the method further comprises the player navigating the unit through a labyrinth by moving the unit in both the x-direction and the y-direction.

5. The method according to claim 1 wherein the method further comprises the player moving the unit in the x-direction by lowering the brain wave frequency to a value that is lower than a value of a brain wave frequency while the player simultaneously moves the unit in the y-direction when the brain wave frequency exceeds 18 Hz.

6. The method according to claim 1 wherein the method further comprises the player winning the game by moving the unit to a segment adjacent to the player.

7. The method according to claim 1 wherein the method further comprises the player losing the game by moving the unit over an edge in the y-direction.

8. The method of claim 1 wherein the method further comprises the first player rolling the unit in a y-direction perpendicular to the x-direction when the brain wave frequency of the first player is at least 18 Hz and the brain wave frequency of the first player is greater than the brain wave frequency of the second player.

9. The method of claim 1 wherein the unit is a magnetic ball.

10. The method of claim 2, wherein the distance (D) is a constant distance.

11. The method of claim 1, wherein the goal area of the first player is situated in the direction of the second player and rolling the unit on top of the playing area in the x-direction toward the goal area of the first player also rolls the unit towards the second player.

* * * * *